United States Patent
Kurth et al.

(12)

(10) Patent No.: US 6,207,144 B1
(45) Date of Patent: Mar. 27, 2001

(54) POLYPEPTIDES WITH INTERLEUKIN-16 ACTIVITY, PROCESS FOR THE PREPARATION AND USE THEREOF

(75) Inventors: Reinhard Kurth, Dreiech; Michael Baier, Frankfurt; Norbert Bannert, Frankfurt; Karin Metzner, Frankfurt; Albrecht Werner, Weinheim; Kurt Lang, Penzberg, all of (DE)

(73) Assignees: Roche Diagnostics, GmbH, Mannheim; Bundesrepublik Deutschland, vertreten durch den Bundesminister fur Gesundheit, Bon, both of (DE)

( * ) Notice: Subject to any disclaimer, the term of this patent is extended or adjusted under 35 U.S.C. 154(b) by 0 days.

(21) Appl. No.: 09/091,405

(22) PCT Filed: Dec. 17, 1996

(86) PCT No.: PCT/EP96/05662

§ 371 Date: Aug. 27, 1998

§ 102(e) Date: Aug. 27, 1998

(87) PCT Pub. No.: WO97/23616

PCT Pub. Date: Jul. 3, 1997

(30) Foreign Application Priority Data

Dec. 22, 1995 (DE) ............... 195 48 295
Jan. 31, 1996 (DE) ............... 196 03 492
Apr. 6, 1996 (DE) ............... 196 13 866
Apr. 6, 1996 (DE) ............... 196 13 886

(51) Int. Cl.$^7$ ............... C12N 15/24; C07K 14/54
(52) U.S. Cl. ............... 424/85.2; 435/383; 435/69.52; 435/69.7; 435/325; 435/252.3; 530/351; 536/23.5
(58) Field of Search ............... 435/69.1, 69.52, 435/69.7, 325, 252.3, 383; 530/351; 536/23.4, 23.5; 434/85.2

(56) References Cited

U.S. PATENT DOCUMENTS 4,624,926 * 11/1986 Inouye et al. ............ 435/253
5,807,712 * 9/1998 Center et al. ............ 435/69.5

FOREIGN PATENT DOCUMENTS 0 736 600   10/1996 (EP) .

OTHER PUBLICATIONS

Cruikshank et al., Proc. Natl. Acd. Sci., vol. 91, pp. 5109–5113, "Molecular and functional analysis of a lymphocyte chemoattractant faxtor: Association of biologic function iwth CD4 expression", 1994.
International Publication No. WO 94/28134, published Dec. 8, 1994.
Center et al., Immunology Today, vol. 17, No. 10, Oct. 1996, pp. 476–481, "Interleukin 16 and its function as a CD4 ligand".
Wu et al., Journal of Allergy and Clinical Immunology, vol. 99, No. 1, part 2, Jan. 1997, "Cloning and functional characterization of the murine CD4 ligand interleukin–16".
Chupp et al., Journal of Allergy and Clinical Immunology, vol. 99, No. 1, part 2, Jan. 1997, Pro–IL–16 is an 80 kDa cytoplasmic protein expressed in blood T–lymphocytes.
Baier et al., Nature, vol. 378, Dec. 7, 1995, pp. 563, "HIV suppression by interleukin 16".

* cited by examiner

Primary Examiner—Lorraine Spector
(74) Attorney, Agent, or Firm—Arent Fox Kintner Plotkin Kahn

(57) ABSTRACT

A nucleic acid which can be used to express a polypeptide with interleukin-16 activity in a prokaryotic or eukaryotic host cell, wherein in the region coding for the said polypeptide the said nucleic acid a) corresponds to the DNA sequence of nucleotides 54–1175 from SEQ ID NO:1 or to its complementary strand, b) hybridizes with the DNA of nucleotide sequence 54–785 from SEQ ID NO:1 under stringent conditions, c) hybridizes with the DNA of nucleotide sequence 786–1175 from SEQ ID NO:1 under stringent conditions and at the 5' end begins with nucleotides 756–785 from SEQ ID NO:1 or a part thereof which codes for part of the sequence of amino acids 235–244 from SEQ ID NO:1 or d) it is a nucleic acid sequence which would hybridize under stringent conditions with the nucleic acid sequences defined by a) or b) without the degeneracy of the genetic code, codes for proteins with improved interleukin-16 activity.

13 Claims, No Drawings

SEQUENCE LISTING

<160> NUMBER OF SEQ ID NOS: 12

<210> SEQ ID NO 1
<211> LENGTH: 1178
<212> TYPE: DNA
<213> ORGANISM: Artificial Sequence
<220> FEATURE:
<221> NAME/KEY: CDS
<222> LOCATION: (54)..(1178)
<220> FEATURE:
<223> OTHER INFORMATION: Description of Artificial Sequence: IL-16

<400> SEQUENCE: 1

```
ttcctcgaga gctgtcaaca caggctgagg aatctcaagg cccagtgctc aag atg        56
                                                            Met
                                                             1 cct agc cag cga gca cgg agc ttc ccc ctg acc agg tcc cag tcc tgt      104
Pro Ser Gln Arg Ala Arg Ser Phe Pro Leu Thr Arg Ser Gln Ser Cys
            5                  10                  15 gag acg aag cta ctt gac gaa aag acc agc aaa ctc tat tct atc agc      152
Glu Thr Lys Leu Leu Asp Glu Lys Thr Ser Lys Leu Tyr Ser Ile Ser
        20                  25                  30 agc caa gtg tca tcg gct gtc atg aaa tcc ttg ctg tgc ctt cca tct      200
Ser Gln Val Ser Ser Ala Val Met Lys Ser Leu Leu Cys Leu Pro Ser
    35                  40                  45 tct atc tcc tgt gcc cag act ccc tgc atc ccc aag gaa ggg gca tct      248
Ser Ile Ser Cys Ala Gln Thr Pro Cys Ile Pro Lys Glu Gly Ala Ser
50                  55                  60                  65 cca aca tca tca tcc aac gaa gac tca gct gca aat ggt tct gct gaa      296
Pro Thr Ser Ser Ser Asn Glu Asp Ser Ala Ala Asn Gly Ser Ala Glu
                70                  75                  80 aca tct gcc ttg gac aca ggg ttc tcg ctc aac ctt tca gag ctg aga      344
Thr Ser Ala Leu Asp Thr Gly Phe Ser Leu Asn Leu Ser Glu Leu Arg
            85                  90                  95 gaa tat aca gag ggt ctc acg gaa gcc aag gaa gac gat gat ggg gac      392
Glu Tyr Thr Glu Gly Leu Thr Glu Ala Lys Glu Asp Asp Asp Gly Asp
        100                 105                 110 cac agt tcc ctt cag tct ggt cag tcc gtt atc tcc ctg ctg agc tca      440
His Ser Ser Leu Gln Ser Gly Gln Ser Val Ile Ser Leu Leu Ser Ser
    115                 120                 125 gaa gaa tta aaa aaa ctc atc gag gag gtg aag gtt ctg gat gaa gca      488
Glu Glu Leu Lys Lys Leu Ile Glu Glu Val Lys Val Leu Asp Glu Ala
130                 135                 140                 145 aca tta aag caa tta gac ggc atc cat gtc acc atc tta cac aag gag      536
Thr Leu Lys Gln Leu Asp Gly Ile His Val Thr Ile Leu His Lys Glu
                150                 155                 160 gaa ggt gct ggt ctt ggg ttc agc ttg gca gga gga gca gat cta gaa      584
Glu Gly Ala Gly Leu Gly Phe Ser Leu Ala Gly Gly Ala Asp Leu Glu
            165                 170                 175
```

-continued

```
aac aag gtg att acg gtt cac aga gtg ttt cca aat ggg ctg gcc tcc    632
Asn Lys Val Ile Thr Val His Arg Val Phe Pro Asn Gly Leu Ala Ser
        180                 185                 190 cag gaa ggg act att cag aag ggc aat gag gtt ctt tcc atc aac ggc    680
Gln Glu Gly Thr Ile Gln Lys Gly Asn Glu Val Leu Ser Ile Asn Gly
195                 200                 205 aag tct ctc aag ggg acc acg cac cat gat gcc ttg gca atc ctc cgc    728
Lys Ser Leu Lys Gly Thr Thr His His Asp Ala Leu Ala Ile Leu Arg
210                 215                 220                 225 caa gct cga gag ccc agg caa gct gtg att gtc aca agg aag ctg act    776
Gln Ala Arg Glu Pro Arg Gln Ala Val Ile Val Thr Arg Lys Leu Thr
                230                 235                 240 cca gag gcc atg ccc gac ctc aac tcc tcc act gac tct gca gcc tca    824
Pro Glu Ala Met Pro Asp Leu Asn Ser Ser Thr Asp Ser Ala Ala Ser
            245                 250                 255 gcc tct gca gcc agt gat gtt tct gta gaa tct aca gca gag gcc aca    872
Ala Ser Ala Ala Ser Asp Val Ser Val Glu Ser Thr Ala Glu Ala Thr
        260                 265                 270 gtc tgc acg gtg aca ctg gag aag atg tcg gca ggg ctg ggc ttc agc    920
Val Cys Thr Val Thr Leu Glu Lys Met Ser Ala Gly Leu Gly Phe Ser
275                 280                 285 ctg gaa gga ggg aag ggc tcc cta cac gga gac aag cct ctc acc att    968
Leu Glu Gly Gly Lys Gly Ser Leu His Gly Asp Lys Pro Leu Thr Ile
290                 295                 300                 305 aac agg att ttc aaa gga gca gcc tca gaa caa agt gag aca gtc cag   1016
Asn Arg Ile Phe Lys Gly Ala Ala Ser Glu Gln Ser Glu Thr Val Gln
                310                 315                 320 cct gga gat gaa atc ttg cag ctg ggt ggc act gcc atg cag ggc ctc   1064
Pro Gly Asp Glu Ile Leu Gln Leu Gly Gly Thr Ala Met Gln Gly Leu
            325                 330                 335 aca cgg ttt gaa gcc tgg aac atc atc aag gca ctg cct gat gga cct   1112
Thr Arg Phe Glu Ala Trp Asn Ile Ile Lys Ala Leu Pro Asp Gly Pro
        340                 345                 350 gtc acg att gtc atc agg aga aaa agc ctc cag tcc aag gaa acc aca   1160
Val Thr Ile Val Ile Arg Arg Lys Ser Leu Gln Ser Lys Glu Thr Thr
355                 360                 365 gct gct gga gac tcc tag                                           1178
Ala Ala Gly Asp Ser
370             375
```

<210> SEQ ID NO 2
<211> LENGTH: 374
<212> TYPE: PRT
<213> ORGANISM: Artificial Sequence
<220> FEATURE:
<223> OTHER INFORMATION: Description of Artificial Sequence: IL-16

<400> SEQUENCE: 2

```
Met Pro Ser Gln Arg Ala Arg Ser Phe Pro Leu Thr Arg Ser Gln Ser
 1               5                  10                  15

Cys Glu Thr Lys Leu Leu Asp Glu Lys Thr Ser Lys Leu Tyr Ser Ile
                20                  25                  30

Ser Ser Gln Val Ser Ser Ala Val Met Lys Ser Leu Leu Cys Leu Pro
            35                  40                  45

Ser Ser Ile Ser Cys Ala Gln Thr Pro Cys Ile Pro Lys Glu Gly Ala
        50                  55                  60

Ser Pro Thr Ser Ser Asn Glu Asp Ser Ala Ala Asn Gly Ser Ala
65                  70                  75                  80

Glu Thr Ser Ala Leu Asp Thr Gly Phe Ser Leu Asn Leu Ser Glu Leu
                85                  90                  95
```

-continued

```
Arg Glu Tyr Thr Glu Gly Leu Thr Glu Ala Lys Glu Asp Asp Gly
            100                 105                 110

Asp His Ser Ser Leu Gln Ser Gly Gln Ser Val Ile Ser Leu Leu Ser
        115                 120                 125

Ser Glu Glu Leu Lys Lys Leu Ile Glu Glu Val Lys Val Leu Asp Glu
130                 135                 140

Ala Thr Leu Lys Gln Leu Asp Gly Ile His Val Thr Ile Leu His Lys
145                 150                 155                 160

Glu Glu Gly Ala Gly Leu Gly Phe Ser Leu Ala Gly Gly Ala Asp Leu
                165                 170                 175

Glu Asn Lys Val Ile Thr Val His Arg Val Phe Pro Asn Gly Leu Ala
            180                 185                 190

Ser Gln Glu Gly Thr Ile Gln Lys Gly Asn Glu Val Leu Ser Ile Asn
        195                 200                 205

Gly Lys Ser Leu Lys Gly Thr Thr His His Asp Ala Leu Ala Ile Leu
210                 215                 220

Arg Gln Ala Arg Glu Pro Arg Gln Ala Val Ile Val Thr Arg Lys Leu
225                 230                 235                 240

Thr Pro Glu Ala Met Pro Asp Leu Asn Ser Ser Thr Asp Ser Ala Ala
                245                 250                 255

Ser Ala Ser Ala Ala Ser Asp Val Ser Val Glu Ser Thr Ala Glu Ala
            260                 265                 270

Thr Val Cys Thr Val Thr Leu Glu Lys Met Ser Ala Gly Leu Gly Phe
        275                 280                 285

Ser Leu Glu Gly Gly Lys Gly Ser Leu His Gly Asp Lys Pro Leu Thr
290                 295                 300

Ile Asn Arg Ile Phe Lys Gly Ala Ala Ser Glu Gln Ser Glu Thr Val
305                 310                 315                 320

Gln Pro Gly Asp Glu Ile Leu Gln Leu Gly Gly Thr Ala Met Gln Gly
                325                 330                 335

Leu Thr Arg Phe Glu Ala Trp Asn Ile Ile Lys Ala Leu Pro Asp Gly
            340                 345                 350

Pro Val Thr Ile Val Ile Arg Arg Lys Ser Leu Gln Ser Lys Glu Thr
        355                 360                 365

Thr Ala Ala Gly Asp Ser
    370
```

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: IL-16

<400> SEQUENCE: 3

```
Arg Lys Leu Thr Pro Glu Ala
  1               5
```

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: IL-16

<400> SEQUENCE: 4

```
Arg Lys Leu Thr Pro Glu
 1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: IL-16

<400> SEQUENCE: 5

Arg Lys Leu Thr Pro
 1               5
```

```
<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: IL-16

<400> SEQUENCE: 6

Arg Lys Leu Thr
 1
```

```
<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: IL-16

<400> SEQUENCE: 7

Arg Lys Leu
 1
```

```
<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: IL-16

<400> SEQUENCE: 8

Leu Thr Pro Glu Ala Met Pro
 1               5
```

```
<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: IL-16

<400> SEQUENCE: 9

Leu Thr Pro Glu Ala Met
 1               5
```

```
<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: IL-16

<400> SEQUENCE: 10
```

```
-continued

Leu Thr Pro Glu Ala
  1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: IL-16

<400> SEQUENCE: 11

Leu Thr Pro Glu
  1

<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence: IL-16

<400> SEQUENCE: 12

Leu Thr Pro
```

POLYPEPTIDES WITH INTERLEUKIN-16 ACTIVITY, PROCESS FOR THE PREPARATION AND USE THEREOF

The invention concerns polypeptides with IL-16 activity, processes for their production and their use.

IL-16 (interleukin-16) is a lymphokine which is also referred to as lymphocyte chemoattracting factor (LCF) or immunodeficiency virus suppressing lymphokine (ISL). IL-16 and its properties are described in WO 94/28134, WO 96/31607 and by Cruikshank, W. W., et al., Proc. Natl. Acad. Sci. USA 91 (1994) 5109–5113 and by Baier, M., et al., Nature 378 (1995) 563. The recombinant production of IL-16 is also described in these references. According to these IL-16 is a protein with a molecular mass of 13,385 D. Cruikshank also found that ISL eluted in a molecular sieve chromatography as a multimeric form with a molecular weight of 50–60 and 55–60 kD. The chemoattractant activity has been attributed to this multimeric form which is a cationic homotetramer (product information AMS Biotechnology Ltd., Europe, Cat. No. 11177186). A homodimeric form of IL-16 with a molecular weight of 28 kD is described by Baier. However, the chemoattractant activity described by Cruikshank et al. in J. Immunol. 146 (1991) 2928–2934 and the activity of recombinant human IL-16 described by Baier are very small.

The object of the present invention is to improve the activity of IL-16 and to provide IL-16 forms which have a low immunogenicity and are advantageously suitable for a therapeutic application.

The object of the invention is achieved by a nucleic acid which can be used to express a polypeptide with interleukin-16 activity in a prokaryotic or eukaryotic host cell wherein the said nucleic acid in the region coding for the said polypeptide a) corresponds to the DNA sequence of nucleotides 54–1175 from SEQ ID NO:1 or to its complementary strand b) hybridizes with the DNA of nucleotide sequence 54–785 from SEQ ID NO:1 under stringent conditions, c) hybridizes with the DNA of nucleotide sequence 786–1175 from SEQ ID NO:1 under stringent conditions and at the 5' end begins with nucleotides 756–785 from SEQ ID NO:1 or a part thereof which codes for part of the sequence of amino acids 235–244 from SEQ ID NO:1 or d) it is a nucleic acid sequence which would hybridize under stringent conditions with the nucleic acid sequences defined by a) or b) without the degeneracy of the genetic code.

In a preferred embodiment the nucleic acid which is defined by b) also additionally hybridizes with the DNA of nucleotides 786–1175 from SEQ ID NO:1.

Such a nucleic acid preferably codes for a polypeptide with improved IL-16 activity, particularly preferably improved natural IL-16 from primates such as human IL-16 or IL-16 of an ape species or of another mammal such as the mouse.

It has surprisingly turned out that IL-16 forms with an N-terminally extended sequence compared to the IL-16 described in WO 94/28134 are still active. Such IL-16 forms even have an increased activity in vivo due to an increased half life.

It has surprisingly turned out that FIG. 2 of WO 94/28134 does not describe the correct sequence of IL-16. The start codon "ATG" does not begin with nucleotide 783 but rather with nucleotide 54. This reading frame results when an A is inserted after nucleotide 156, a C is inserted after nucleotide 398 and a G is inserted after nucleotide 780. The correct reading frame is shown in SEQ ID NO:1. This sequence also shows further differences to FIG. 2 of WO 94/28134. However, these are only nucleotide substitutions (e.g. 313 G into A, 717 C into A). The nucleic acid according to the invention also codes for a polypeptide which can be processed during its production. Such a polypeptide which is thus extended compared to the known IL-16 from WO 94/28134 exhibits an improved activity. Monomeric IL-16 with improved activity has a molecular weight of 13.9–39 kD, preferably ca. 15–35 kD and is thus about three times as large as the C-terminal IL-16 fragment described in WO 94/28134.

The sequence of IL-16 can differ to a certain extent from protein sequences coded by such DNA sequences. Such sequence variations of IL-16 muteins may be amino acid substitutions, deletions or additions. However, the amino acid sequence of IL-16 is preferably at least 75% and particularly preferably at least 90% identical to the amino acid sequence of SEQ ID NO:1. Variants of parts of the amino and of the nucleic acid sequences SEQ ID NO:1/SEQ ID NO:2 are for example described in the International Application WO 96/31607 and the German Patent Application 195 47 933.5.

Particularly preferred IL-16 muteins with improved activity begin at the N-terminus with the amino acids 235–244 from SEQ ID NO:1/2 or a part thereof. Particularly preferred N-termini are described in SEQ ID NO:3–12.

In a preferred embodiment the IL muteins with improved activity can be truncated at the C-terminus by preferably 1–20 amino acids.

Nucleic acids within the sense of the invention are understood for example as DNA, RNA and nucleic acid derivatives and analogues. Preferred nucleic acid analogues are those compounds in which the sugar phosphate backbone is replaced by other units such as e.g. amino acids. Such compounds are referred to as PNA and are described in WO 92/20702. Since PNA-DNA bonds are for example stronger than DNA-DNA bonds, the stringent conditions described above are not applicable to PNA-DNA hybridization. However, suitable hybridization conditions are described in Wo 92/20703.

The term IL-16 is understood within the sense of the invention as a polypeptide with the activity of IL-16 or preferably with an improved activity. IL-16 preferably exhibits the stated action in the test procedure described in the International Application WO 96/31607 or stimulates cell division according to WO 94/28134.

IL-16 binds to $CD4^+$ lymphocytes and can suppress the replication of viruses such as for example HIV-1, HIV-2 and SIV. The function of IL-16 is not limited by its presentation in the MHC complex.

In particular IL-16 exhibits one or several of the following properties:

binding to T cells via the CD4 receptor, stimulation of the expression of the IL-2 receptor and/or HLA-DR antigen on $CD4^+$ lymphocytes, stimulation of the proliferation of T helper cells in the presence of IL-2, suppression of the proliferation of T helper cells stimulated with anti-CD3 antibodies, suppression of the replication of viruses preferably of HIV-1, HIV-2 or SIV.

The term "hybridize under stringent conditions" means that two nucleic acid fragments hybridize with one another under standardized hybridization conditions as described for example in Sambrook et al., "Expression of cloned genes in *E. coli*" in Molecular Cloning: A laboratory manual (1989), Cold Spring Harbor Laboratory Press, New York, USA. Such conditions are for example hybridization in 6.0×SSC at about 45° C. followed by a washing step with 2×SSC at 50° C. In order to select the stringency the salt concentration in the washing step can for example be chosen between 2.0× SSC at 50° C. for low stringency and 0.2×SSC at 50° C. for high stringency. In addition the temperature of the washing step can be varied between room temperature, ca. 22° C., for low stringency and 65° C. for high stringency.

IL-16 is preferably produced recombinantly in prokaryotic or eukaryotic host cells. Such production processes are described for example in WO 94/28134 and the WO 96/31607 which are also for this purpose a subject matter of the disclosure of the present invention. However, in order to obtain the forms according to the invention of IL-16 by recombinant production in a defined and reproducible manner, additional measures have to be taken beyond the processes for recombinant production familiar to a person skilled in the art.

Recombinant IL-16 can be produced by methods familiar to a person skilled in the art. For this a DNA is firstly produced which is able to produce a protein which has the activity of IL-16. The DNA is cloned in a vector which can be transferred into a host cell and can be replicated there. Such a vector contains operator elements in addition to the IL-16 sequence which are necessary for the expression of the DNA sequence. This vector which contains the IL-16 sequence and the operator elements is transferred into a vector which is able to express the DNA of IL-16. The host cell is cultured under conditions which are suitable for the amplification of the vector and IL-16 is isolated. In this process suitable measures ensure that the protein can adopt an active tertiary structure in which it exhibits IL-16 properties.

In this process it is not necessary that the expressed protein contains the exact IL-16 amino acid sequence from SEQ ID NO:1. Proteins are also suitable which contain essentially the same sequence and exhibit analogous properties. Proteins in which N-terminal amino acids are deleted are especially suitable.

The nucleic acid sequence of the protein can also be modified. Such modifications are for example:

modification of the nucleic acid in order to introduce various recognition sequences of restriction enzymes to facilitate the steps of ligation, cloning and mutagenesis
  modification of the nucleic acid to incorporate preferred codons for the host cell
  extension of the nucleic acid by additional operator elements in order to optimize expression in the host cell.

The protein is preferably expressed in microorganisms in particular in prokaryotes and in this case in *E. coli*.

The expression vectors must contain a promoter which allows expression of the protein in the host organism. Such promoters are known to a person skilled in the art and are for example the lac promoter (Chang et al., Nature 198 (1977) 1056), trp promoter (Goeddel et al., Nuc. Acids Res. 8 (1980) 4057), $\lambda_{PL}$ promoter (Shimatake et al., Nature 292 (1981) 128) and T5 promoter (U.S. Pat. No. 4,689,406). Synthetic promoters such as for example the tac promoter (U.S. Pat. No. 4,551,433) are also suitable. Coupled promoter systems are equally suitable such as for example the T7-RNA polymerase/promoter system (Studier et al., J. Mol. Biol. 189 (1986) 113). Hybrid promoters composed of a bacteriophage promoter and the operator region of the microorganism (EP-A 0 267 851) are also suitable. An effective ribosome binding site is necessary in addition to the promoter. In the case of *E. coli* this ribosome binding site is referred to as the Shine-Dalgarno (SD) sequence (Sambrook et al., "Expression of cloned genes in *E. coli*" in Molecular Cloning: A laboratory manual (1989) Cold Spring Harbor Laboratory Press, New York, USA).

In order to improve expression it is possible to express the protein as a fusion protein. In this case a DNA sequence which codes for the N-terminal part of an endogenous bacterial protein or another stable protein is usually fused to the 5' end of the sequence coding for IL-16. Examples of this are for example lacZ (Phillips and Silhavy, Nature 344 (1990) 882–884), trpE (Yansura, Meth. Enzymol. 185 (1990) 161–166).

After expression of the vector which is preferably a biologically functional plasmid or a viral vector, the fusion proteins are preferably cleaved with enzymes (Carter P. in Ladisch, M. R. et al. eds., Protein Purification: From Molecular Mechanisms to Large-Scale Processes, ACS Symposium Series No. 427, American Chemical Society (1990) 181–193). Examples of cleavage sites are the IgA protease cleavage site (WO 91/11520, EP-A 0 495 398) the ubiquitin cleavage site (Miller et al., Bio/Technology 7 (1989) 698) the enterokinase cleavage site (Maroux et al., J. Biol. Chem. 241 (1971) 5031) and factor Xa cleavage site (Nagai et al., Nature 309 (1984) 810).

The proteins expressed in this manner in bacteria are obtained in the usual manner by disrupting the bacteria and isolating the protein.

In a further embodiment it is possible to secrete the proteins from the microorganisms as active proteins. For this a fusion product is preferably used which is composed of the signal sequence that is suitable for secretion of proteins in the host organisms used and of the nucleic acid that codes for the protein. In this case the protein is either secreted into the medium (in gram-positive bacteria) or into the periplasmatic space (in gram-negative bacteria). It is expedient to insert a cleavage site between the signal sequence and the sequence coding for IL-16 which allows cleavage of the protein either during processing or in an additional step. Such signal sequences are derived for example from ompA (Ghrayeb et al., EMBO J. 3 (1984) 2437), phoA (Oka et al., Proc. Natl. Acad. Sci. USA 82 (1985) 7212).

The vectors additionally contain terminators. Terminators are DNA sequences that signal the end of a transcription process. They are usually characterized by two structural features: a reversely repetitive G/C-rich region which can form a double helix intramolecularly as well as a number of U (or T) residues. Examples are the main terminator in the DNA of the phages fd (Beck and Zink, Gene 16 (1981) 35–38) and rrnB (Brosius et al., J. Mol. Biol. 148 (1981) 107–127).

In addition the expression vectors usually contain a selectable marker in order to select transformed cells. Such selectable markers are for example the resistance genes for ampicillin, chloramphenicol, erythromycin, kanamycin, neomycin and tetracyclin (Davies et al., Ann. Rev. Microbiol. 32 (1978) 469). Selectable markers which are equally suitable are the genes for essential substances for the biosynthesis of substances necessary for the cell such as e.g. histidine, tryptophan and leucine.

Numerous suitable bacterial vectors are known. Vectors have for example been described for the following bacteria: *Bacillus subtilis* (Palva et al., Proc. Natl. Acad. Sci. USA 79 (1982) 5582), *E. coli* (Aman et al., Gene 40 (1985) 183; Studier et al., J. Mol. Biol. 189 (1986) 113), *Streptococcus*

*cremoris* (Powell et al., Appl. Environ. Microbiol. 54 (1988) 655), *Streptococcus lividans* and *Streptomyces lividans* (U.S. Pat. No. 4,747,056).

Further genetic engineering methods for the production and expression of suitable vectors are described in J. Sambrook et al., Molecular cloning: a laboratory manual (1989), Cold Spring Harbor Laboratory Press, New York, N.Y.

In addition to prokaryotic microorganisms it is also possible to express recombinant IL-16 in eukaryotes (such as for example CHO cells, yeast or insect cells). The yeast system or insect cells are preferred as a eukaryotic expression system. Expression in yeast can be achieved by means of three types of yeast vectors: (integrating $YI_p$ (yeast integrating plasmids) vectors, replicating $YR_p$ (yeast replicon plasmids) vectors and episomal $YE_p$ (yeast episomal plasmids) vectors. More details of this are described for example in S. M. Kingsman et al. Tibtech 5 (1987) 53–57.

The invention in addition concerns a prokaryotic or eukaryotic host cell which is transformed or transfected with a nucleic acid which codes for an IL-16 polypeptide according to the invention in such a way that the host cell expresses the said polypeptide. Such a host cell usually contains a biologically functional nucleic acid vector, preferably a DNA vector, a plasmid DNA, which contains this nucleic acid.

In addition the invention concerns human interleukin-16 or interleukin-16 from primates, preferably human IL-16 with improved activity obtainable as the product of a prokaryotic or eukaryotic expression which is essentially free of other human proteins. IL-16 is a protein which is present as a monomer or as a multimer composed of monomeric IL-16 (also denoted subunits in the following). The molecular weight of a monomeric IL-16 subunit is preferably 13.9–39 kD, particularly preferably 15–35 kD. A monomeric IL-16 polypeptide that has a molecular weight of 15–30 kD is additionally preferred which cannot be cleaved into further subunits.

It has surprisingly turned out that the nucleic acid and the protein sequence of IL-16 described in WO 94/28134 do not correspond to the natural human sequences. It is merely an IL-16 fragment with a non-natural N-terminus. However, a protein is preferably used for a therapeutic application which is either identical to the natural protein or only differs slightly from the natural protein and/or at least exhibits comparable and preferably improved activity and immunogenicity. Surprisingly it was found that natural unprocessed or not yet secreted IL-16 is a larger protein with a molecular weight of 13.9–39 kD contrary to the previous assumption. Its sequence is described in the sequence protocols.

The nucleic acid sequence of IL-16 can, within the scope of the invention contain deletions, mutations and additions. A part of the 5' end in the order of 20–240, preferably 20–90 codons, preferably 20–50 codons, especially preferably ca. 35, 75, 234, 237 or 239 codons is preferably deleted. An IL-16 (monomeric form, subunit) that is coded by such a nucleic acid then has a molecular weight of ca. 13.9–39 kD. This monomeric form of IL-16 can be multimerized in a preferred embodiment. The activity of IL-16 can be increased in this manner. Such multimeric forms are preferably dimeric, tetrameric or octameric forms.

In a further embodiment the polypeptides of the invention can additionally contain a defined proportion of metal ions, the number of metal ions per subunit being preferably 0.5 to 2.

Numerous metal ions are suitable as metal ions within the sense of the invention which are added in a defined amount during the production of multimeric forms of IL-16. It has turned out that alkaline earth metals as well as elements of the side groups are suitable. Alkaline earth metals, cobalt, zinc, selenium, manganese, nickel, copper, iron, magnesium, calcium, molybdenum and silver are particularly suitable. The ions may be monovalent, divalent, trivalent or tetravalent. Divalent ions such as Cu(II) ions are particularly preferred. The ions are preferably added as solutions of $MgCl_2$, $CaCl_2$, $MnCl_2$, $BaCl_2$, $LiCl_2$, $Sr(NO_3)_2$, $Na_2MoO_4$, $AgCl_2$ or Cu(II) acetate.

Such multimeric forms, the production thereof in the presence of metal ions, and forms of IL-16 containing metal ions are described in the German Patent Application No. 195 47 933.5.

The polypeptide according to the invention can be prepared in such a way that a prokaryotic or eukaryotic host cell which has been transformed or transfected with a nucleic acid sequence as claimed in claims 1 or 2, is cultured under suitable nutrient conditions and the desired polypeptide is optionally isolated. If it is intended to produce the polypeptide in vivo in the context of a gene therapy treatment, the polypeptide is of course not isolated from the cell.

A further subject matter of the invention is a pharmaceutical composition which contains a polypeptide according to the invention in an amount and/or specific activity which is sufficient for a therapeutic application as well as optionally a pharmaceutically suitable diluent, adjuvant and/or carrier.

The polypeptides according to the invention are especially suitable for treating pathological states which are caused by viral replication, in particular retroviral replication, and for immunomodulation. Such therapeutic applications are also described in WO 94/28134 and WO 96/31607. Diagnostic test procedures are also described in the latter.

The polypeptides according to the invention can also be used for immunosuppression. This immunosuppression is preferably achieved by an inhibition of the helper function of the $TH_0$ and/or $TH_1$ and $TH_2$ cells. Hence the polypeptides according to the invention are of therapeutic value in all diseases in which an immunodysregulatory component is postulated in the pathogenesis and in particular a hyperimmunity. Diseases which can be treated by IL-16 in cardiology/angiology are for example myocarditis, endocarditis and pericarditis, in pulmonology for example bronchitis, asthma, in haematology autoimune neuropenias and transplant rejections, in gastroenterology chronic gastritis, in endocrinology diabetes mellitus type I, in nephrology glomerulonephritis, rheumatic diseases, diseases in ophthalmology, in neurology such as multiple sclerosis and eczemas in dermatology. The polypeptides according to the invention can be used in particular for autoimmune diseases, allergies and to avoid transplant rejections.

The invention furthermore concerns the use of the nucleic acids according to the invention within the context of gene therapy. Retroviral or non-viral vector systems are for example suitable vector systems for this.

In addition the invention concerns a polyclonal or monoclonal anti-IL-16 antibody or an immunoactive fragment thereof as well as processes for the production of such antibodies and their use for the determination of IL-16 and for determining viral infections in eukaryotic cells and in particular in mammalian cell material. Virus-activated mammalian cells and in particular T cells can also be determined with IL-16. The production of such an antibody is carried out by immunization with a polypeptide according to the invention which preferably corresponds essentially to the amino acid sequence 1–244 from SEQ ID NO:1/2 and which binds to such a peptide. An antibody is preferably used that does not bind to the polypeptide of amino acid sequence 245–374 from SEQ ID NO:1/2. The production of such an antibody is carried out according to processes familiar to a person skilled in the art.

The following examples and publications as well as the sequence protocol further elucidate the invention the protective scope of which results from the patent claims. The processes described are to be understood as examples that still describe the object of the invention even after modifications.

EXAMPLE 1
Cloning, expression and purification of IL-16
1.1 RNA isolation $5 \times 10^7$ PBMC (from humans or monkeys) were cultured for 48 hours with 10 µg/ml concanavalin A and 180 U/ml IL-2. In order to prepare the RNA, the cells were washed once with PBS and subsequently lysed with 5 ml denaturation solution (RNA isolation kit, Stratagene). The lysate was kept on ice for 15 min after addition of 1 ml Na acetate, 5 ml phenol and 1 ml chloroform/isoamyl alcohol (24:1). The aqueous phase was subsequently mixed with 6 ml isopropanol in order to precipitate the RNA and stored for 2 hours at –20° C. The precipitate was finally washed once with pure ethanol and dissolved in 150 µl $H_2O$. The yield was determined photometrically and was 120 µg.

1.2 cDNA synthesis

The mixture for the cDNA synthesis contained 10 µg RNA, 0.2 µg oligo-dT, 13 mM DTT and 5 µl bulk first strand reaction mix (first strand cDNA synthesis kit, Pharmacia) in an amount of 15 µl. The mixture was incubated for 1 hour at 37° C. and subsequently stored at –20° C. for later use.

The amplification, cloning of IL-16 cDNA and production of an expression clone is carried out as described in WO 94/28134 or WO 96/31607 taking the modified sequence into consideration. For the purification according to example 3 an N-terminal elongation by several histidine residues is necessary.

EXAMPLE 2
10 $l$ fermentation of an *E. coli* expression clone for IL-16 and high pressure disruption Precultures are set up from stock cultures (plate smear or ampoules stored at –20° C.) which are incubated at 37° C. while shaking. The inoculation volume into the next higher dimension is 1–10 vol. % in each case. Ampicillin (50–100 mg/l) is used in the preculture and main culture to select against plasmid loss.

Enzymatically digested protein and/or yeast extract as a N- and C-source as well as glycerol and/or glucose as an additional C-source are used as nutrients. The medium is buffered to pH 7 and metal salts are added at physiologically tolerated concentrations to stabilize the fermentation process. The fermentation is carried out as a feed batch with a mixed yeast extract/C sources dosage. The fermentation temperature is 25–37° C. The dissolved partial oxygen pressure ($pO_2$) is kept at <20% by means of the aeration rate, r.p.m. regulation and dosage rate.

The growth is determined by determining the optical density (OD) at 528 nm. The expression of IL-16 is induced by means of IPTG. After a fermentation period of ca. 10 hours the biomass is harvested by centrifugation at OD standstill. The biomass is taken up in 50 mM sodium phosphate, 5 mM EDTA, 100 mM sodium chloride, pH 7 and is disrupted at 1000 bar by means of a continuous high pressure press. The suspension obtained in this manner is centrifuged again and the supernatant which contains the dissolved IL-16 is processed further.

EXAMPLE 3
Purification of recombinant human IL-16

550 ml lysis supernatant in 50 mM sodium phosphate, 5 mM EDTA, 100 mM NaCl, pH 7.2 was admixed with 55 ml 5 M NaCl, 60 mM $MgCl_2$, pH 8.0, stirred for 30 minutes and subsequently centrifuged for 30 minutes at 20,000 g. 400 ml of the supernatant was taken up on a nickel-chelate Sepharose column (V=60 ml; Pharmacia), which had previously been loaded with 30 µMol $NiCl_2$/ml gel and equilibrated with 50 mM sodium phosphate, 0.2 M NaCl, pH 8.0. The column was subsequently washed with 300 ml 50 mM sodium phosphate, 0.5 M NaCl, pH 7.0 and the IL-16 fusion protein was then eluted with a gradient of 0 M to 300 mM imidazole, pH 7.0 in 50 mM sodium phosphate, 0.1 M NaCl, pH 7.0 (2* 0.5 gradient volumes). Fractions containing IL-16 were identified by means of SDS-PAGE and pooled.

300 mg of the fusion protein obtained in this way was dialysed at 4° C. against 20 l 20 mM imidazole, pH 5.5 and subsequently centrifuged for 30 minutes at 20,000 g in order to remove turbidities. The supernatant of the centrifugation was subsequently adjusted to pH 8.5 with NaOH, admixed with 0.3 g thrombin (Boehringer Mannheim GmbH) and incubated for 4 hours at 37° C. Subsequently the cleavage mixture was adjusted to pH 6.5 with HCl and the conductivity was set to 1.7 mS by dilution with $H_2O$. The sample was applied to a Q-Sepharose FF column (45 ml; Pharmacia) which had previously been equilibrated with 20 mM imidazole, pH 6.5. IL-16 was eluted using a gradient of 0 to 0.3 N NaCl in 20 mM imidazole, pH 6.5. Fractions containing IL-16 were identified by means of SDS-PAGE, pooled and the identity of IL-16 was confirmed by means of mass analysis and N-terminal sequence analysis.

The IL-16 obtained in this manner had a purity of more than 95% in SDS-PAGE under reducing conditions. The analytical Superdex 75 FPLC column (Pharmacia) was eluted with 25 mM Na phosphate, 0.5 M NaCl, 10% glycerol, pH 7.0 at a flow rate of 1 ml/min. The amount of protein applied in a volume of 100 to 150 µl was 1.5 to 15 µg protein. Detection was at 220 nm.

A Vydac, Protein & Peptide C18, 4×180 mm column was used to analyse purity by means of RP-HPLC. It was eluted with a linear gradient of 0% to 80% B (solvent B: 90% acetonitrile in 0.1% TFA; solvent A: 0.1% TFA in $H_2O$) within 30 minutes at a flow rate of 1 ml/min. Detection was at 220 nm.

List of references

Aman et al., Gene 40 (1985) 183

Baier, M., et al., Nature 378 (1995) 563

Beck and Zink, Gene 16 (1981) 35–58

Brosius et al., J. Mol. Biol. 148 (1981) 107–127

Carter P. in Ladisch, M. R. et al., eds., Protein Purification: From Molecular Mechanisms to Large-Scale Processes, ACS Symposium Series No. 427, American Chemical Society (1990) 181–193

Chang et al., Nature 198 (1977) 1056

Cruikshank, W. W., et al., J. Immunol. 146 (1991) 2928–2934

Cruikshank, W. W., et al., Proc. Natl. Acad. Sci. USA 91 (1994) 5109–5113

Davies et al., Ann. Rev. Microbiol. 32 (1978) 469

German Patent Application NO. 195 47 933.5

EP-A 0 267 851

EP-A 0 495 398

Ghrayeb et al., EMBO J. 3 (1984) 2437

Goeddel et al., Nuc. Acids Res. 8 (1980) 4057

Kingsman, S. M., et al, Tibtech 5 (1987) 53–57

Mack et al., Analyt. Biochem. 200 (1992) 74–80

Maroux et al., J. Biol. Chem. 241 (1971) 5031

Miller et al., Bio/Technology 7 (1989) 698

Nagai et al., Nature 309 (1984) 810

Oka et al., Proc. Natl. Acad. Sci. USA 82 (1985) 7212

Palva et al., Proc. Natl. Acad. Sci. USA 79 (1982) 5582
Phillips and Silhavy, Nature 344 (1990) 882–884
Powell et al., Appl. Environ. Microbiol. 54 (1988) 655
Sambrook et al., "Expression of cloned genes in *E. coli*" in Molecular Cloning: A laboratory manual (1989), Cold Spring Harbor Laboratory Press, New York, USA
Shimatake et al., Nature 292 (1981) 128
Studier et al., J. Mol. Biol. 189 (1986) 113
U.S. Pat. No. 4,551,433
U.S. Pat. No. 4,689,406
U.S. Pat. No. 4,747,056
WO 91/11520
WO 92/20702
WO 92/20703
WO 94/28134
WO 96/31607
Yansura, Meth. Enzymol. 185 (1990) 161–166

What is claimed is:

1. An isolated nucleic acid encoding a polypeptide with interleukin-16 activity, wherein said nucleic acid can be expressed in a prokaryotic or eukaryotic host cell, comprising a nucleic acid sequence selected from the group consisting of
   a) the sequence of nucleotides 54–1175 from SEQ ID NO: 1 or a subsequence thereof which is truncated at the 5'-end by 20–240 codons and
   b) a sequence which encodes amino acids 1–374 from SEQ ID NO: 2 or a fragment thereof which is truncated at the C-terminus by 1–20 amino acids.

2. The nucleic acid according to claim 1, wherein the polypeptide with interleukin-16 activity is from a primate.

3. The nucleic acid according to claim 1, further comprising, upstream of said nucleic acid sequence, a sequence encoding a signal sequence suitable for secretion of the polypeptide.

4. A prokaryotic or eukaryotic host cell which is transformed or transfected with a nucleic acid according to claim 1, wherein the host cell expresses said polypeptide with interleukin-16 activity.

5. A vector comprising a nucleic acid according to claim 1.

6. A complementary nucleic acid sequence which is complementary to any of the nucleic acid sequences of claim 1.

7. A purified polypeptide with interleukin-16 activity, wherein the polypeptide can be expressed using a nucleic acid comprising a nucleic acid sequence selected from the group consisting of
   a) the sequence of nucleotides 54–1175 from SEQ ID NO: 1 or a subsequence thereof which is truncated at the 5'-end by 20–240 codons and
   b) a sequence which encodes amino acids 1–374 from SEQ ID NO: 2 or a fragment thereof which is truncated at the C-terminus by 1–20 amino acids,
wherein the polypeptide has a molecular weight of 13.9 to 39 kD.

8. The polypeptide according to claim 7, wherein the polypeptide is a product of prokaryotic or eukaryotic expression and is at least 95% pure.

9. A purified polypeptide with interleukin-16 activity, wherein the polypeptide is a multimer composed of subunits, and wherein each of said subunits is the polypeptide according to claim 7.

10. The polypeptide according to claim 9, wherein the polypeptide is composed of up to four subunits.

11. A process for the production of a polypeptide according to claim 7, comprising the steps of:
   transforming or transfecting a prokaryotic or eukaryotic host cell with a nucleic acid comprising a nucleic acid sequence selected from the group consisting of
   a) the sequence of nucleotides 54–1175 from SEQ ID NO: 1 or a subsequence thereof which is truncated at the 5'-end by 20–240 codons and
   b) a sequence which encodes amino acids 1–374 from SEQ ID NO: 2 or a fragment thereof which is truncated at the C-terminus by 1–20 amino acids,
   culturing the host cell in a culture medium, and
   isolating the polypeptide from the host cell or the culture medium.

12. The process according to claim 11, wherein the host cell is cultured in the presence of metal ions.

13. A pharmaceutical composition, comprising a polypeptide according to claim 7 in combination with a pharmaceutically acceptable carrier.

* * * * *